United States Patent
Gagnon et al.

(10) Patent No.: US 6,922,859 B2
(45) Date of Patent: Aug. 2, 2005

(54) TABLE FOR POSITIONING A PATIENT FOR A MEDICAL PROCEDURE ON A BREAST

(75) Inventors: Mario Gagnon, Montreal (CA); Christian Pilon, Montreal (CA)

(73) Assignee: Art Advanced Research Technologies Inc., St-Laurent (CA)

( * ) Notice: Subject to any disclaimer, the term of this patent is extended or adjusted under 35 U.S.C. 154(b) by 0 days.

(21) Appl. No.: 10/306,724

(22) Filed: Nov. 29, 2002

(65) Prior Publication Data

US 2004/0103477 A1 Jun. 3, 2004

(51) Int. Cl.$^7$ .......................... A61G 13/00; A61G 13/12
(52) U.S. Cl. .................... 5/601; 5/110; 5/621; 5/186.1; 5/623; 378/209
(58) Field of Search .......................... 5/601, 632, 731, 5/735, 621, 600, 110, 112, 111, 114, 186.1, 187, 623; 378/37, 209

(56) References Cited

U.S. PATENT DOCUMENTS

| | | | |
|---|---|---|---|
| 3,165,630 A | * | 1/1965 | Bielat et al. .................. 378/37 |
| 3,464,069 A | * | 9/1969 | Bien ............................. 5/110 |
| 3,973,126 A | | 8/1976 | Redington et al. |
| 4,341,222 A | | 7/1982 | Gardineer et al. |
| 4,596,384 A | * | 6/1986 | Blosser ......................... 5/613 |
| 5,095,569 A | * | 3/1992 | Glenn ........................... 5/490 |
| 5,289,520 A | | 2/1994 | Pellegrino et al. |
| 5,409,497 A | | 4/1995 | Siczek et al. |
| 5,415,169 A | | 5/1995 | Siczek et al. |
| 5,564,438 A | | 10/1996 | Merchant |
| 5,569,266 A | | 10/1996 | Siczek |
| 5,609,152 A | | 3/1997 | Pellegrino et al. |
| 5,661,860 A | * | 9/1997 | Heitz ............................ 5/632 |
| 6,185,768 B1 | * | 2/2001 | Schlechter ..................... 5/632 |
| 6,195,580 B1 | | 2/2001 | Grable |
| 6,367,104 B1 | * | 4/2002 | Falbo et al. ................... 5/601 |
| 6,419,390 B1 | * | 7/2002 | Landis-Lowell ............ 378/209 |
| 2002/0061090 A1 | | 5/2002 | Lindsrom et al. |

FOREIGN PATENT DOCUMENTS

| | | |
|---|---|---|
| DE | 10026792 | 12/2001 |
| EP | 845242 A2 | 6/1998 |
| FR | 2 653 005 | 4/1991 |
| GB | 2 277 664 A | 6/1993 |
| WO | WO 98/55013 | 12/1998 |
| WO | WO 01/35829 A1 | 5/2001 |

* cited by examiner

*Primary Examiner*—Alexander Grosz
(74) *Attorney, Agent, or Firm*—Alexandra Daoud; James Anglehart; Ogilvy Renault

(57) ABSTRACT

There is provided a table for positioning a patient for a medical procedure on a breast, the table comprising: a solid frame surrounding a perimeter of the table; and a membrane-like contour surface for a surrounding breast area, wherein the surface comprises an aperture for the breast to be pendantly suspended therethrough, and the surface is adjusted to a shape of the patient's body. Preferably, the membrane-like contour surface covers the entire surface area of the table. Alternatively, it can be limited to a section that will cover an area from approximately the bottom of the rib cage to the collar bone when the patient is lying face down on the table.

11 Claims, 3 Drawing Sheets

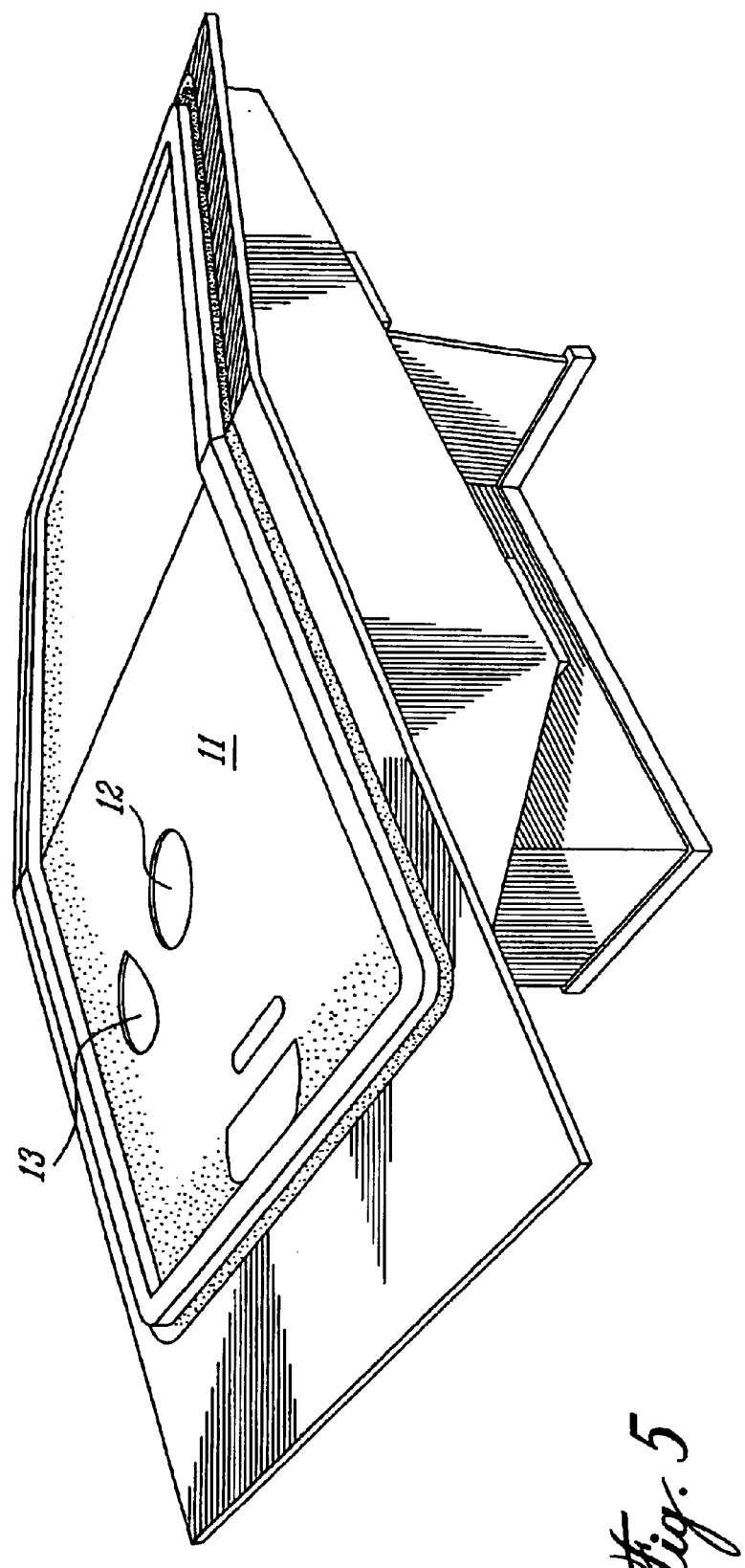

TABLE FOR POSITIONING A PATIENT FOR A MEDICAL PROCEDURE ON A BREAST

CROSS-REFERENCE TO RELATED APPLICATION

This application is related to U.S. patent application entitled "Method and Apparatus for Positioning the Arm of a Patient While on a Table for a Medical Procedure on a Breast" filed Dec. 12, 2002, as Ser. No. 10/317,215, the specification of which is hereby incorporated by reference. The application is also related to U.S. patent applications entitled "Method and Apparatus for Positioning a patient on a Table for a Medical Procedure on a Breast" filed on Nov. 8, 2002 as Ser. No. 10/290,476, and "Method and Apparatus for Optical Imaging" filed on Nov. 8, 2002 as Ser. No. 10/290,485, the specifications of which are hereby incorporated by reference.

FIELD OF THE INVENTION

The invention relates to a table for positioning a patient when performing a medical procedure on a breast. More specifically, it relates to features of the table that can improve the volume of breast tissue accessible beneath the table to the medical equipment.

BACKGROUND OF THE INVENTION

Certain medical procedures, such as breast biopsies, must be done with the patient in a face down prone position. There are also imaging and scanning procedures that are done in a prone position. There are several variations of tables that currently exist for these procedures.

A major concern for these types of procedures is breast coverage. Breast coverage is to be understood as the volume of tissue that can be contained between a pair of parallel plates that are used to compress and scan the breast. Research has shown that a large proportion of breast tumors are found in the surrounding axilla region adjacent to the breast. Therefore, it is vital that the tools used to diagnose and treat breast tumors can access this area accordingly.

The tables that exist in the state of the art are standard, thick tables with a hole cut out to allow the breast to be pendantly suspended therethrough. The thickness of the table prevents the equipment located below the table to properly access the breast tissue such that the desired regions of interest are reached. In order to access the maximum breast tissue, the equipment must be allowed to be as close as possible to the rib cage.

Therefore, there is a need to provide a table such that a maximum volume of breast tissue can be accessed by the equipment located beneath it.

SUMMARY OF THE INVENTION

Accordingly, an object of the present invention is to provide maximum access to breast and axilla tissue via an aperture on a table, for medical equipment located beneath the table.

According to a first broad aspect of the present invention, there is provided a table for positioning a patient for a medical procedure on a breast, the table comprising: a solid frame surrounding a perimeter of the table; and a membrane-like contour surface for a surrounding breast area, wherein the surface comprises an aperture for the breast to be pendantly suspended therethrough, and the surface is adjusted to a shape of the patient's body.

Preferably, the membrane-like contour surface covers the entire surface area of the table. Alternatively, it can be limited to a section that will cover an area from approximately the bottom of the rib cage to the collar bone when the patient is lying face down on the table.

Also preferably, the membrane-like contour surface is a resilient, elastomeric material that is stretched across the frame and conforms to the shape of the body. Alternatively, it can be a plastic contour that is substantially proportional to the patient's size and proportions. The plastic contour can be chosen from a family of different shapes and sizes that can all be fitted onto the table.

The aperture can be located centrally with respect to the length of the table such that the patient is facing one direction if the left breast is in the aperture and an opposite direction if the right breast is in the aperture. Alternatively, the aperture can be moved in location such that the patient is always facing the same direction. The aperture can be part of a detachable portion of the contour surface such that attachment means allow it to be removed and placed at a different location, or simply opened and closed.

A second aperture can be provided for the arm adjacent to the breast to be exposed through the table. The arm aperture may also be moved in location. Armrests may be provided beneath the table for the arm that is exposed via the arm aperture. Head rests and feet rests may also be provided.

BRIEF DESCRIPTION OF THE DRAWINGS

These and other features, aspects and advantages of the present invention will become better understood with regard to the following description and accompanying drawings wherein:

FIG. 5 is a perspective view of the embodiment of FIG. 3.

DETAILED DESCRIPTION OF THE PREFERRED EMBODIMENT

Figure 1:
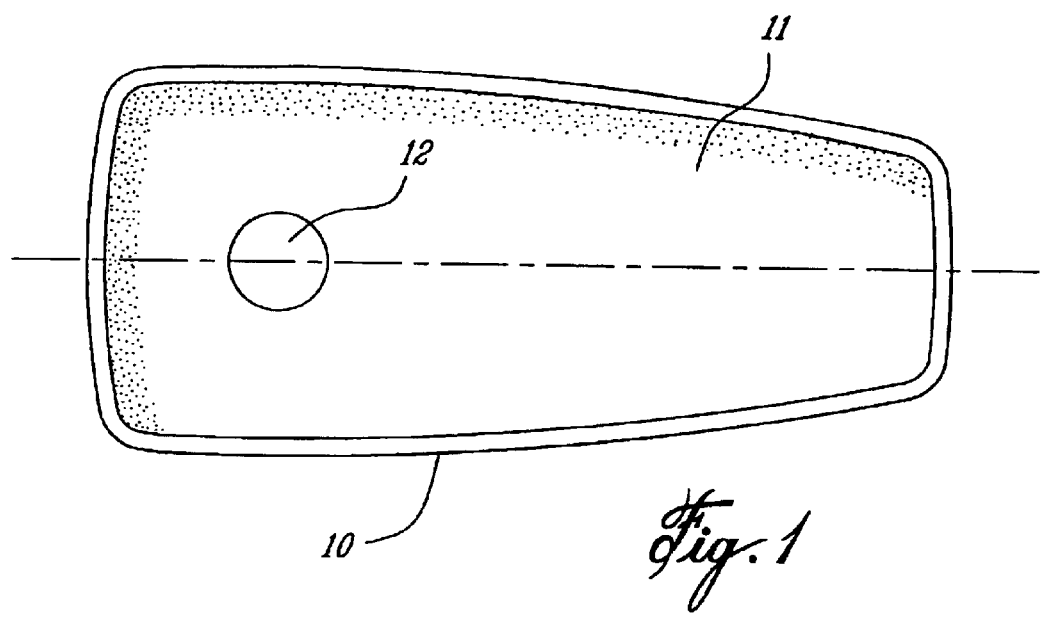
FIG. 1 is an embodiment of the soft table.

FIG. 1 shows a first embodiment for the soft table. A solid frame 10 surrounds the perimeter of the table. A fabric 11 is stretched across the frame to form the entire surface of the table. The patient is supported by the fabric 11 while lying in a prone position. The table conforms to the shape of the patient's body. In the figure, the fabric 11 is a resilient, elastomeric type of material, such as neoprene. The neoprene is resilient and withstands a lot of weight such that a heavy person does not sink down lower than a lighter person. Essentially, the fabric 11 can be any type of material that can conform to the shape of the body and withstand weight without the possibility of tearing. It can also be a material that is already adjusted to the shape of the body, but is thin enough to provide the membrane-like attribute.

An aperture 12 is present in the fabric such that a breast undergoing a medical procedure can be pendantly suspended therethrough, and wherein an area underneath the breast aperture 12 is unobstructed so as to provide access to the breast for scanning equipment, biopsy equipment, stabilizing plates, or any such type of medical equipment used to perform a procedure on a breast. The advantage of the soft table is that the fabric 11 provides a very thin membrane between the rib cage of the patient and any equipment provided beneath the table. This means more of the breast is exposed beneath the table via the aperture 12. For example, parallel stabilizing plates that are beneath the table and compress the breast from a variety of angles can access a larger volume of breast tissue when the layer between the rib cage and the equipment is thin. This constitutes better breast coverage.

One, embodiment for the table consists in having the table wide enough such that the aperture 12 is located substantially centrally across the width, and the patient lies off-center on the table, depending on whether a left or a right breast is exposed through the aperture 12. This is seen in FIG. 1.

Figure 2:
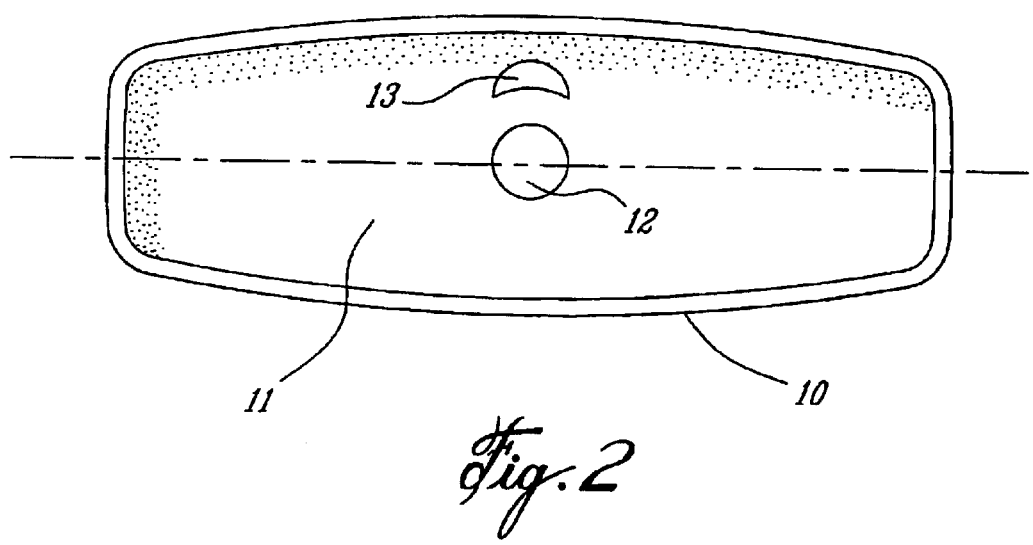
FIG. 2 is an alternative embodiment of the soft table.

Another embodiment for the table, as seen in FIG. 2, is to have the breast aperture 12 located in a central portion of the length of the table and have an area for the legs and torso of the patient on either side of the central portion. If the medical procedure is to be done on a left breast, the patient's legs and torso occupy one end of the table and if the medical procedure is for the right breast, the patient's legs and torso occupy the other end of the table.

The advantages of the embodiments seen in FIGS. 1 and 2 are that one table can accommodate all procedures, the equipment beneath the table never has to be moved because the breast will always be in the same location, and the table can be setup against a wall, which manages floor space efficiently.

An arm aperture 13 can be seen on FIG. 2. The arm aperture 13 is located next to the breast aperture 12 such that the arm adjacent to the breast undergoing the medical procedure can go through the table and reside below it.

Figure 3:
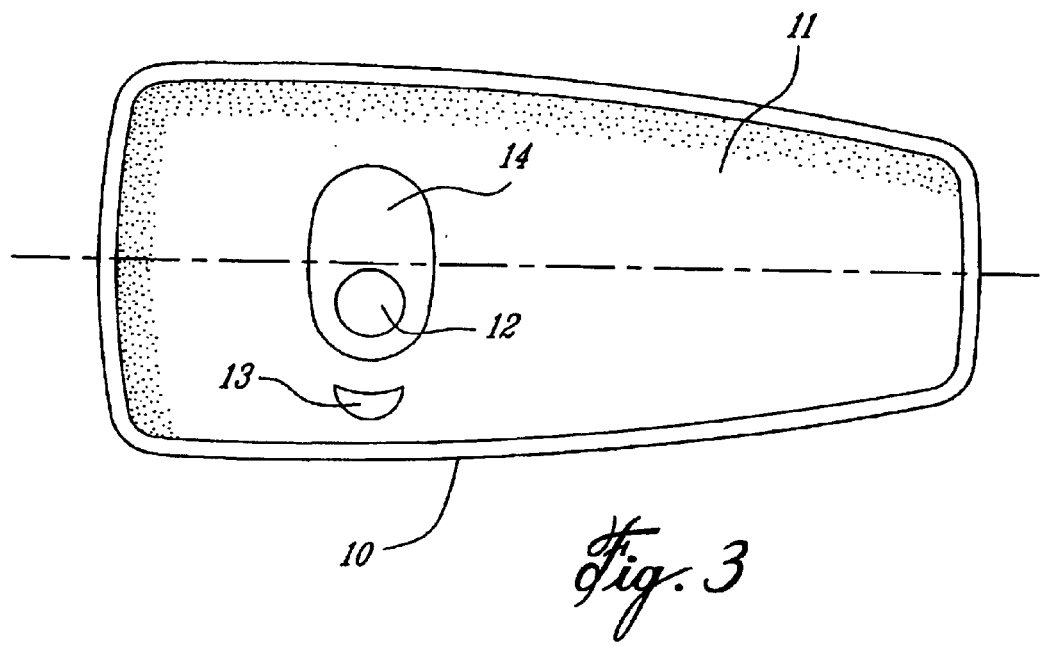
FIG. 3 is an alternative embodiment of the soft table.

Yet another embodiment to accommodate a medical procedure on a left or right breast consists in having the aperture 12 for the breast in a portion of the fabric 11 that is detachable from the rest of the table, such as that seen in FIG. 3. The attachment means may be Velcro™, zippers, snaps, etc. A large aperture 14 in the fabric 11 is provided such that two smaller apertures can fit into it. A smaller piece of fabric containing the single aperture 12 for the breast is attached to the table via the attachment means. The detachable portion can be detached, rotated by substantially 180°, and reattached such that the aperture 12 has been flipped across a central axis of the table.

Alternatively, the detachable portion may consist of the entire surface of the table. That is, the table comprises two layers, one with a large aperture 14 and a second layer beneath it with the smaller aperture 12 for the breast. The attachment means are located along the frame 10 of the table. When the two layers are overlaid, the smaller aperture 12 fits within the larger aperture 14 to provide the hole for the breast to be exposed. The layer with the larger aperture 14 is the upper surface and the layer with the smaller aperture 12 is the lower surface. To move the location of the aperture 12 for the breast, the underneath layer is detached, flipped horizontally or rotated by 180°, and reattached.

Also alternatively, the aperture may be provided via single detachable portions in the fabric that can simply be opened and closed using the attachment means.

Although the apertures shown in the figures are substantially circular in shape, the aperture may be oval, rectangular, or pear-shaped in order to expose the axilla region adjacent to the breast. This region must often be accessed by either imaging or biopsy equipment in the case of medical procedures on breasts.

Furthermore, there may be a string surrounding a contour of the aperture that provides adjustment in size to the breast aperture. The string allows the opening of the adjustment to be adjusted as a function of breast size. It also allows the aperture to be properly closed and sealed around the breast for the analysis. Alternatively, if the breast apertures are provided via detachable means, apertures of varying sizes may be provided proportional to the size of the patent.

The arm aperture 13 seen in FIG. 3 allows the shoulder to be lowered such that it rests at a lower level than the rest of the body. It also provides better breast coverage, especially for the axilla region adjacent to the breast, and is useful when the aperture is of a non-circular shape, as described above.

As for the breast aperture 12, the arm aperture 13 may also be moved from a left to a right side of the table, and vice versa. The embodiments described above for changing the location of the breast aperture 12 are also valid for changing the location of the arm aperture 13.

An armrest (not shown) can also be provided beneath the table in order to support the forearm and elbow of the arm exposed through the arm aperture 13. This way, the height of the shoulder can be adjusted by positioning the forearm and elbow at a desired location on the armrest. Better breast coverage can be achieved this way. The armrest can be moveable such that when the location of the arm aperture 13 is changed, the armrest can be switched to the opposite side of the table. The armrest can also be fixed in the case of an arm aperture 13 of fixed location. Alternatively, there can be two armrests beneath the table, one for each side.

Yet another feature of the soft table consists in a strapping system that allows the adjustment of certain elements, such as head resting area angle and depth, for example. A foot rest may also be provided to elevate the patient's feet and provide additional comfort.

Figure 4:
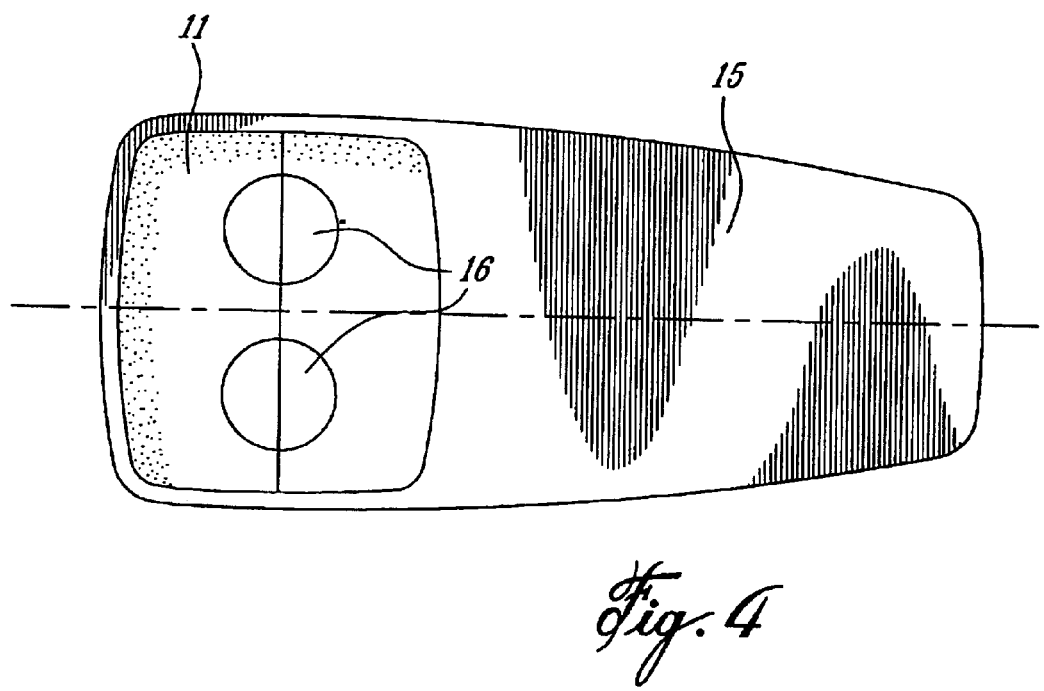
FIG. 4 is an embodiment of the hybrid table.

Alternatively, FIG. 4 shows a hybrid model of the soft table and hard table. A rigid portion 15 supports the legs and lower torso, while a soft and flexible portion 11 supports the upper torso. Therefore, the patient feels a better sense of security by having the rigid support and better breast coverage is obtained by having the soft portion. A rigid headrest (not shown) is provided to complement the support provided to the legs and lower torso and complete the feeling of security. All of the features and embodiments described above with respect to the soft table can be implemented with the hybrid table.

FIG. 4 also has two apertures 16 for the breast. Only one of these apertures 16 is opened at a time. Attachment means such as Velcro™, zippers, snaps, etc, are used to close the aperture while it is not in use. Alternatively, one of the apertures 16 is used for the breast while the other is used for the arm. In this case, both apertures 16 are opened at the same time. When a left breast is undergoing examination, the right aperture is for the breast and the left aperture is for the arm. When a right breast is undergoing examination, the left aperture is for the breast and the right aperture is for the arm. The patient lies slightly off-center on the table. This embodiment is also possible with the soft table described above. That is, it is not necessary to have the rigid portion 15 in order to have the apertures configured as they are in FIG. 4.

What is essential for the table is that the surrounding breast area be placed in a contour that is either pre-shaped to the body or conforms to the body once the body is placed into it. For example, a thin rigid plastic molding can be used that substantially fits to the proportions of the body. Either each body is molded individually, or a large variety of moldings exist for different body shapes and proportions. Therefore, each patient gets a molding that fits her shape from approximately the rib cage to the collar bone. The molded plastic acts as the membrane that will support the patient and allow access to the breast and surrounding axilla region.

FIG. 5 is a perspective view of the soft table with the breast and arm apertures placed as they are in FIG. 3. From the figure, it can be seen that the material used for supporting the body is thin and conforms to the shape of the body. The thin material is stretched across the supporting frame to cover the entire surface of the platform. The back part of the table is inclined to provide the feet at a lower level than the upper body.

It can be appreciated that the table can also be configured such that the supporting platform is only for the upper body. That is, the platform supports the torso from the waist up and the patient remains either in a standing or kneeling position next to the platform.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A table for positioning a patient for a medical procedure on a breast, the table comprising:

a membrane-like contour surface comprised of a resilient, elastomeric fabric adapted to support the area of a patient's body surrounded the breast area, wherein said surface comprises an aperture for the breast to be pendantly suspended therethrough, and said surface is adjusted to a shape of the patient's body, and wherein an area underneath the membrane-like contour surface is unobstructed so as to provide access to said breast pendantly suspended therethrough; and a support for supporting a remainder of the patient's body.

2. A table for positioning a patient for a medical on a breast, the table comprising:

a membrane-like contour surface comprised of a thin rigid plastic molding adapted to support the area of a patient's body surrounding the breast area, wherein said surface comprised an aperture for the breast to be pendantly suspended therethrough, and said surface is adjusting to a shape of the patient's body, and wherein an area underneath the membrane-like contour surface is unobstructed so as provide access to said breast pendantly suspended therethrough; and a support for supporting a remainder of the patient's body.

3. A table as claimed in claim 1 or 2, wherein said membrane-like contour surface and said support are integrated together.

4. A table as claimed in claim 1 or 2, wherein said aperture is located centrally with respect to a first and a second end of said table such that a patient's legs and torso will lie on said first end of said table for a medical procedure on a left breast and on said second end of said table for a medical procedure on a right breast.

5. A table as claimed in claim 1 or 2, wherein a location of said aperture can be modified to accommodate a left and a right breast such that a patient's legs and torso reside at a same end of said table for a procedure on one of said left breast and said right breast.

6. A table as claimed in claim 5, wherein said aperture is comprised within a detachable portion of said membrane-like contour surface mounted on said table via attachment means, and wherein said detachable portion is rotated by substantially 180° and reattached in order to provide said aperture on an opposite side of said table.

7. A table as claimed in claim 6, wherein said attachment means are provided using hook and loop type fasteners.

8. A table as claimed in claim 1 or 2, further comprising a second aperture adjacent to said aperture such that an arm of said patient adjacent to said breast can be exposed and rest below said table.

9. A table as claimed in claim 8, wherein, said second aperture is comprised within a detachable portion of said contour surface mounted on said table via attachment means, and wherein said portion is rotated by substantially 180° and reattached in order to provide said second aperture on an opposite side of said table.

10. A table as claimed in claim 8, further comprising an arm rest below said table such that an arm exposed through said second aperture can rest on said arm rest.

11. A table as claimed in claim 1 or 2, further comprising an adjustable head rest.

* * * * *